United States Patent [19]

Stapp

[11] 3,963,757

[45] June 15, 1976

[54] PROCESS FOR THE PREPARATION OF LACTONES

[75] Inventor: Paul R. Stapp, Bartlesville, Okla.

[73] Assignee: Phillips Petroleum Company, Bartlesville, Okla.

[22] Filed: Aug. 21, 1972

[21] Appl. No.: 282,253

Related U.S. Application Data

[63] Continuation-in-part of Ser. No. 888,867, Dec. 29, 1969, abandoned.

[52] U.S. Cl. ........................... 260/343.6; 260/343.5; 260/617 R; 260/618 D; 260/632 R
[51] Int. Cl.² ............... C07D 307/32; C07D 309/30

[58] Field of Search ...................... 260/343.6, 343.5

[56] References Cited

OTHER PUBLICATIONS

Houben–Weyl; Methoden der Organischen Chemie. Verlag, Stuttgart 1963 Band VI/2 p. 656.

*Primary Examiner*—Alton D. Rollins

[57] ABSTRACT

Lactones are produced by reacting water and a cyanide with haloalkanols in the presence of a phosphine promoter.

12 Claims, No Drawings

PROCESS FOR THE PREPARATION OF LACTONES

This is a continuation-in-part of application Ser. No. 888,867 filed December 29, 1969 now abandoned. This invention relates to use of a phosphine promoter process for the preparation of lactones to increase the yield of these lactones.

The lactones that can be produced by the process of this invention are known in the art. For example 2-methyl-4-butyrolactone is disclosed in Chemical Abstracts, 64, 6614a (1966).

It now has been found that the yield of lactones can be increased by reacting water and a cyanide with haloalkanols in the presence of a trihydrocarbylphosphine promoter.

Accordingly, it is an object of this invention to provide a promoter which will increase the yield of lactone obtained when reacting water, a cyanide, and a haloalkanol.

Other objects, aspects and advantages will become apparent to one skilled in the art upon consideration of the following disclosure and appended claims.

The formation of lactones in the presence of the promoter of this invention can be represented as follows:

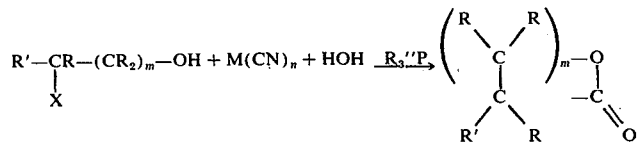

wherein R' is hydrogen or alkyl, cycloalkyl, or aryl or combinations thereof such as for example alkaryl, aralkyl, etc., having from 1 to 8 carbon atoms per R' group; R is hydrogen or alkyl having from 1 to 3 carbon atoms per R group; the total number of carbon atoms in all R groups per molecule is not greater than 6; R'' is alkyl, aryl, cycloalkyl or combinations thereof such as aralkyl, alkaryl, and the like, having from 1 to 8 carbon atoms in each group; R''$_3$P is a phosphine promoter; M is an alkali or alkaline earth metal; HCN can replace all but a catalytic amount of M(CN)$_n$; X is a halogen; n is the integer 1 or 2; and m is the integer 2 or 3.

Preferably, M is beryllium, magnesium, calcium, strontium, barium lithium, sodium, potassium or rubidium and X is chlorine, bromine, fluorine, or iodine.

Specific examples of haloalkanols that can be employed in the process of this invention are: 3-chlorobutanol, 3-fluorobutanol, 3-bromobutanol, 3-iodobutanol, 3-fluoroundecanol, 3-iodo-5-methyldecanol, 3-bromo-2,3-dimethyl-4-ethyloctanol, 4-bromo-2,3,3,4,6-pentamethyl-2-undecanol, 5-bromo-2-methyl-3-hexanol, 3-chloro-3-cyclopentylpropanol, 3-bromo-3-cyclooctylpropanol, 3-chloro-3 -phenylpropanol, 3-chloro-4-phenylbutanol, 3-chloro-5-phenylpentanol, 3-chloro-3-(3,5-dimethylphenyl)-propanol, 3-chloro-3-(4-methylphenyl)hexanol, 3-bromo-2,2-dimethyl-3-(4-methylcyclohexyl)heptanol, and 3-bromo-6-cyclopentyl-2,3-dipropylhexanol, 4-chlorobutanol, 4-bromobutanol, 4-iodobutanol, 4-fluorobutanol, 4-bromododecanol, 4-iodo-6-methylundecanol, 4-bromp-2,3-dimethyl-5-methylnonanol, 5-bromo-2,3,3,4,7-pentamethyl-2-dodecanol, 6-bromo-2-methyl-3-heptanol, 4-chloro-4-cyclooctylbutanol, 4-chloro-4-cyclopentylbutanol, 4-chloro-4-phenylbutanol, 4-chloro-5-phenylpentanol, 4-fluoro-6-phenylhexanol, 4-iodo-4-(3,5-dimethylphenyl)butanol, 4-iodo-4-(3-methylphenyl)heptanol, 4-bromo-2,3-dimethyl-4-( 4-methylcyclohexyl)octanol, 4-fluoro-7-cyclopentyl-2,4-dipropylheptanol, and the like, and mixtures thereof.

Specific examples of lactones that are produced by the process of this invention are 2-methyl-4-butyrolactone, 2,4-dimethyl-4butyrolactone, 2-ethyl-2-methyl-3-propyl-4-butyrolactone, 3,4-dipropyl-2-methyl-4-butyrolactone, 2-octyl-4-butyrolactone, 2-cyclopentyl-4-butyrolactone, 2-cyclooctyl-4-butyrolactone, 2-phenyl-4-butyrolactone, 2-phenylethyl-4-butyrolactone, 2-(4-ethylphenyl)-4-butyrolactone, 2-(3-cyclopentylpropyl)-4-butyrolactone, 2-(4-ethylcyclohexyl)-4-butyrolactone, 2-(3-ethylhexyl)-4-ethyl-3-propyl-4-butyrolactone, 2-methyl-5-valerolactone, 2,4-dimethyl-5-valerolactone, 2-ethyl-2-methyl-3-propyl-5-valerlactone, 3,4-dipropyl-2-methyl-5-valerolactone, 2-octyl-5-valerolactone, 2-cyclopentyl-5-valerolactone, 2-cyclooctyl-5-valerolactone, 2-phenyl-5-valerolactone, 2-phenylethyl-5-valerolactone, 2-(4-ethylphenyl)-5-valerolactone, 2-(3-cyclopentylpropyl)-5-valerolactone, 2(4-ethylcyclohexyl)-5-valerolactone, 2-(3-ethylhexyl)-5-ethyl-3-propyl-5-valerolactone, and the like, and mixtures thereof.

The equivalent ratio of M(CN)$_n$ to haloalkanol generally ranges from 0.5:1 to 5:1, preferably from 1:1 to 3:1. HCN can replace all but a catalytic amount of the metal cyanide, i.e., at lest 0.001 equivalents of M(CN)$_n$ can be employed per equivalent of haloalkanol wherein the remaining amount of cyanide (-CN) is provided by the HCN to be within the above indicated range. One equivalent of M(CN)$_n$ equals 1/n moles of M(CN)$_n$.

In general, about 0.5 to 5 moles of water are employed for each mole of haloalkanol, preferably in the range of 1 to 3 moles of water per mole of haloalkanol.

The trihydrocarbylphosphine promoters of this invention have the formula R''$_3$P where R'' is as defined previously. The amount of phosphine which is used as a promoter to achieve the improved yield of lactone can vary depending on reactants, reaction conditions, etc., but will usually be in the range of about 0.001 to about 0.1, preferably 0.001 to 0.015, mols of phosphine per mole of haloalkanol. Examples of suitable phosphines are: trimethylphosphine, triphenylphosphine, tri(4-ethylphenyl)phosphine, tri-n-butylphosphine, methyldi(phenyl)phosphine, di(cyclohexyl)octylphosphine, di(n-octyl)-2,4-dimethylphenylphosphine, 2-methylcyclopentyldi(isopropyl)phosphine, tri(2-phenylethyl)phosphine, or triethylphosphine.

Generally, the reaction temperature ranges from 150° to 250°C and the reaction is carried out under pressure sufficient to maintain the reactants substantially completely in the liquid phase. Preferably, the pressure ranges from about 0.5 to about 50 atmospheres, including atmospheric pressure.

A polar diluent which is substantially nonreactive to the reaction environment can be employed if desired, and can comprise as much as 95 weight percent of the total reaction mixture. Examples of suitable diluents include acetonitrile, propionitrile, dimethylformamide, dimethyl sulfoxide, sulfolane, N-methylpyrrolidone, diethyl ether, tetrahydropyran, tetrahydrofuran, benzene, toluene, xylene, methyl ethyl ketone, acetone, methyl isobutyl ketone, cyclohexanone, cyclododecanone, and the like.

Reaction times sufficient to carry out the desired degree of converson are employed. Generally, the reaction time ranges from about 10 minutes to about 48 hours.

The process can be carried out either batchwise or continuously. The product then can be recovered and isolated by any method known in the art for the recovery of lactones. For example, the product can be fractionally distilled.

The lactones produced according to the process of this invention are useful compositions. For example, 4-butyrolactone is disclosed to be an activator for the base catalyzed polymerization of 2-pyrrolidone according to the disclosure of U.S. Pat. No. 2,809,958. Lactones such as 4-butyrolactone and 2-methyl-4-butyrolactone are disclosed to impart butter-like flavor when added to margarine according to U.S. Pat. No. 2,819,169.

The advantages of using a trihydrocarbylphosphine as a promoter according to this invention are further illustrated by the following examples. The reactants and proportions and other specific conditions are presented as being typical and should not be construed to limit the invention unduly.

EXAMPLE I

A 1-liter stainless steel autoclave was charged with 3-chloro-1-butanol (108.5 g., 1.0 mole), potassium cyanide (97.5 g., 1.5 moles), triphenylphosphine (2g., 0.0076 mole), acetonitrile (250 ml.) and water (10 ml.). After flushing with nitrogen, the autoclave was pressured to 200 psig with nitrogen and maintained at 200°C for 4 hours with stirring. The autoclave was then vented, the product mixture dissolved in ether, the etheral mixture washed with water and filtered through diatomaceous earth. The ether layer was dried over anhydrous magnesium sulfate, and filtered. Ether and acetonitrile were distilled from the product mixture and the residue, 76.8 g., was analyzed by gas-liquid chromatography indicating a 48% yield (% of theory) of 2-methyl-4-butyrolactone.

EXAMPLE II

The procedure of Example I was followed with the exception that triphenylphosphine was not employed. Analysis of the product mixture by gas-liquid chromatography indicated a 20.1% yield (% of theory) of 2-methyl-4-butyrolactone.

Comparing Example I to Example II it can be seen that the yield of 2-methyl-4-butyrolactone was increased from 20.1% yield to 48% yield by reacting the constituents in the presence of triphenylphosphine.

Although this invention has been described in considerable detail, it must be understood that such detail is for the purpose of illustration only and that many variations and modifications can be made by one skilled in the art without departing from the scope and spirit thereof.

What is claimed is:

1. A process for the preparation of a lactone represented by the formula

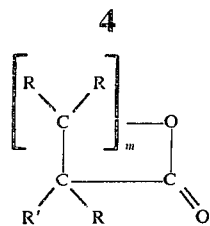

wherein a cyanide repesented by the formula $M(CN)_n$ is reacted with a haloalkanol represented by the formula

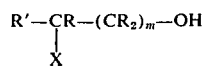

in the presence of water and a phosphine promoter having the formula $R''_3P$ in which formulae $R'$ is hydrogen, alkyl, cycloalkyl, aryl, alkaryl or aralkyl having from 1 to 8 carbon atoms per $R'$ group; R is hydrogen or alkyl having from 1 to 3 carbon atoms per R group, the total number of carbon atoms in all R groups per molecule is not greater than 6; $R''$ is alkyl, aryl, cycloalkyl, aralkyl or alkaryl having from 1 to 8 carbon atoms in each group; M is an alkali or alkaline earth metal, X is a halogen; n is 1 or 2 and m is 2 or 3.

2. A process according to claim 1 wherein the equivalent ratio of $M(CN)_n$ to said haloalkanol ranges from 0.5:1 to 5:1 and the mole ratio of water to said haloalkanol ranges from 0.5:1 to 5:1.

3. A process according to claim 2 wherein HCN replaces the $M(CN)_n$.

4. A process according to claim 3 wherein the equivalent ratio of $M(CN)_n$ to said haloalkanol is at least 0.001:1 wherein the remaining amount of cyanide (-CN) is provided by HCN.

5. A process according to claim 1 wherein said reaction is carried out at a temperature ranging from about 150° to about 250°C, under a pressure sufficient to maintain the resulting reactants substantially completely in the liquid phase, and for a time ranging from about 10 minutes to about 48 hours.

6. A process according to claim 1 wherein X is chlorine, fluorine, bromine, or iodine and M is Be, Mg, Ca, Sr, Ba, Li, Na, K, or Rb.

7. A process according to claim 1 wherein said reaction is carried out in the presence of a polar diluent.

8. A process according to claim 7 wherein said polar diluent is acetonitrile.

9. A process according to claim 1 wherein said haloalkanol is 3-chloro-1-butanol and said cyanide is KCN.

10. A process according to claim 1 wherein said lactone is 2-methyl-4-butyrolactone.

11. A process according to claim 1 wherein the trihydrocarbylphosphine promoter is in the range of about 0.001 to about 0.1 mols of trihydrocarbylphosphine promoter per mole of haloalkanol.

12. A process according to claim 1 wherein the trihydrocarbylphosphine promoter is one of trimethylphosphine, triphenylphosphine, tri(4-ethylphenyl)phosphine, tri-n-butylphosphine, methyldi(phenyl)phosphine, di(cyclohexyl)octylphosphine, di(n-octyl)-2,4-dimethylphenylphosphine, 2-methylcyclopentyldi(isopropyl)phosphine, tri(2-phenylethyl)phosphine, or triethylphosphine.

* * * * *